(12) United States Patent
Chapman et al.

(10) Patent No.: US 6,399,817 B1
(45) Date of Patent: Jun. 4, 2002

(54) PROCESS FOR PREPARING (METH) ACRYLIC ACID

(75) Inventors: Josefina Tseng Chapman, Norristown; James Clarence Day, North Wales, both of PA (US); Donald Alan Ebert, Houston, TX (US); Thomas Albert Kaminski, Houston, TX (US); Robert Michael Mason, Houston, TX (US); Chorng-Shyuan Tsay, Maple Glen, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 09/516,668

(22) Filed: Mar. 1, 2000

Related U.S. Application Data

(60) Provisional application No. 60/122,985, filed on Mar. 5, 1999.

(51) Int. Cl.[7] ............................ C07C 51/16; C07C 51/42
(52) U.S. Cl. ........................................ 562/545; 562/600
(58) Field of Search .................................. 562/545, 600

(56) References Cited

U.S. PATENT DOCUMENTS

| 4,925,981 A | * | 5/1990 | Shimizu et al. |
| 5,196,578 A | * | 3/1993 | Karagano et al. |
| 5,315,037 A | | 5/1994 | Sakamoto et al. |
| 5,785,821 A | | 7/1998 | Sakamoto et al. |
| 5,910,607 A | * | 6/1999 | Sakakura et al. |

FOREIGN PATENT DOCUMENTS

| EP | 0 551 111 | 1/1993 |
| GB | 2 146 636 A | 4/1985 |
| JP | 5-246941 | 9/1993 |

* cited by examiner

*Primary Examiner*—Paul J. Killos
(74) *Attorney, Agent, or Firm*—Alan Holler

(57) ABSTRACT

This invention relates to a process for preparing acrylic acid which utilizes an aqueous stream which includes recycled wastewater, at least part of which is stripped of undesirable components in a stripping column prior to being recycled to an acrylic acid absorber.

8 Claims, 3 Drawing Sheets

PROCESS FOR PREPARING (METH) ACRYLIC ACID

This application claims benefit of provisional application 60/122,985, filed Mar. 5, 1999.

This invention relates to a process for preparing (meth) acrylic acid. In particular, the invention relates to a process for preparing (meth)acrylic acid which utilizes an aqueous stream which includes recycled wastewater in the process to separate product (meth)acrylic acid from a mixed product gas.

Acrylic acid is generally prepared by the catalytic oxidation of at least one hydrocarbon material. For instance, acrylic acid may be prepared from propylene and/or acrolein in a one or two step process. In a first step propylene is oxidized in the presence of oxygen, diluent inert gases, water vapor, and appropriate catalysts to produce acrolein according to equation (I):

$$C_3H_6 + O_2 \Rightarrow C_2H_3CHO + H_2O + \text{heat} \quad (I).$$

The acrolein is then oxidized, in a second step, in the presence of oxygen, diluent inert gases, water vapor, and appropriate catalysts to form acrylic acid according to equation (II):

$$C_2H_3CHO + \tfrac{1}{2}O_2 \Rightarrow C_2H_3COOH + \text{heat} \quad (II).$$

The acrolein may be provided as starting material in a one step reaction (II) to produce acrylic acid.

Alternatively, propane may be used as a starting material. The propane is oxidized using appropriate catalysts, for instance, as described in U.S. Pat. No. 5,380,933 to form product acrylic acid.

Methacrylic acid is similarly prepared by catalytic oxidation of isobutylene and/or isobutane.

The acrylic acid prepared using such catalytic oxidation reactions is present in a mixed product gas exiting the reactor. Generally, the mixed product gas is cooled and is contacted with an aqueous stream in an absorption tower, thereby providing an aqueous acrylic acid solution which is then dehydrated in a distillation step to provide a crude acrylic acid solution. The crude acrylic acid solution can be used to produce various acrylic esters or be further purified to provide various grades of purified acrylic acid which can then be further utilized, for instance in the production of super absorbent polymer products.

Typically in chemical manufacturing processes, including such processes for the production of acrylic acid, a large waste load is generated. Such waste load usually takes the form of waste product gases and waste water streams. Waste product gases may be generated at several points in the acrylic acid manufacturing process. Of particular interest is the remainder of the mixed product gas emerging from the absorber which has had product acrylic acid absorbed from it upon contact with the aqueous stream in the absorber. This remainder of the mixed product gas, known as the absorber waste gas or absorber off-gas, typically undergoes some sort of waste treatment such as thermal oxidation, incineration, or catalytic oxidation before being released to the air so as to comply with applicable environmental requirements.

Wastewater is also generated in the acrylic acid production process as well as in other manufacturing processes. A typical acrylic acid production facility may generate up to two pounds of wastewater per pound of acrylic acid produced, depending on the particular process used. Of particular interest is the wastewater recovered in dehydration processes, such as in the dehydration of acrylic acid. Generally such wastewater also must be treated in some manner to comply with applicable environmental standards before being released into the environment. Consequently, since treatment and disposal of waste gases and wastewater constitutes a significant expense for the acrylic acid manufacturer alternative uses and treatments which add value to the manufacturing process and/or reduce expenses is a constant goal to such manufacturers.

Several methods have been developed in the art to meet this goal. It is known in the art to recycle at least a portion of the absorber off-gas back to the reactor(s). This recycle serves several purposes including providing inert diluent gas and steam to the reactant composition, and reducing wastewater generated by the process by reducing the amount of steam that is fed to the process. Furthermore, small amounts of unreacted propylene and acrolein contained in the off-gas are given another chance to react and thereby improve the overall acrylic acid yield by increasing conversions of propylene and acrolein.

Recycle of certain generated wastes in an acrylic acid process for reuse in the process absorbing step has been taught in the art. For instance, Japanese Patent Application Kokai (Laid Open) No. 246941/1993 teaches recycle of a recovered acetic acid solution for reuse as an absorbent in an acrylic acid absorption tower. However, the application states that acrylic acid recovery is inefficient in the absorber because no solvent and substantially no acrylic acid is present. U.S. Pat. No. 5,785,821 discloses wastewater recycle to the absorber of an acrylic acid process wherein the recycled wastewater stream has a specific composition of acetic acid (3–10 wt %), acrylic acid (0.5–5.0 wt %), and distillation solvent (0.01–0.5 wt %). Such a recycle stream, containing these specific amounts of acetic acid, acrylic acid and distillation solvent is said to enable collection of acrylic acid in the absorber at a high efficiency.

However, one problem envisioned with recycle of wastewater is that the recycled wastewater may contain an unacceptable concentration of undesirable components such as volatile organic compounds (VOC). Such high concentrations of undesirable components in the recycled wastewater stream can lead to a higher waste concentration, e.g., acetic acid and organic distillation solvent, in the absorber off-gas. Consequently, when some or all of an absorber off-gas is recycled to the reactor it will contain a higher level of undesirable components. Such materials may be detrimental to the catalytic oxidation reactions which form acrolein and/or acrylic acid in the reactor. In particular, it is believed that activity of the oxidation catalysts may be reduced by the presence of the higher level of volatile organic components. Furthermore, certain organic, such as toluene, may actually compete with starting materials so that less starting materials are reacted and more by-products show up in the acrylic acid product.

The preparation and isolation of methacrylic acid proceeds by similar steps. Consequently, methacrylic acid manufacturers suffer from similar problems.

The present inventors have now discovered that by stripping the wastewater of undesirable components using a stripping gas including process waste gas overcomes the problem of unsuitable levels of undesirable components being recycled to the absorber. Furthermore, the invention enables obtaining additional value from process wastewater and waste gas streams. This is done while maintaining a suitable acrylic acid collection efficiency in the absorber.

Accordingly, a novel process for preparing acrylic acid is described herein wherein the following advantages are provided:

(1) a decreased amount of undesirable components in the absorber off-gas leading to a decreased amount of potentially harmful components recycled back to the reactor;

(2) additional value is obtained from process waste gas streams by using them to strip process wastewater streams;

(3) stripped wastewater having a lower level of components potentially harmful to the catalytic reactions in the reactor are recycled to the absorber for acrylic acid absorption thereby reducing the wastewater load in the facility;

(4) stripping gas streams sent to thermal oxidizers for treatment have a higher concentration of organic material from the stripping process, thereby reducing the fuel requirement of the thermal oxidizer.

In one aspect of the present invention, there is provided a process for preparing (meth)acrylic acid, including the steps of: (A) feeding to an absorption tower (i) a mixed product gas from the catalytic oxidation of at least one hydrocarbon material with a molecular oxygen containing gas, and (ii) an aqueous stream including recycled wastewater and less than 3.0 percent by weight acetic acid; (B) contacting the mixed product gas with the aqueous stream in the absorption tower to form an aqueous (meth)acrylic acid stream; and (C) feeding the aqueous (meth)acrylic acid stream to a distillation column, wherein it is subjected to azetropic distillation in the presence of at least one distillation solvent to form a (meth)acrylic acid solution substantially free of water.

In a second aspect of the present invention, there is provided a process for preparing (meth)acrylic acid, including the steps of (A) feeding to an absorption tower a mixed product gas from the catalytic oxidation of at least one hydrocarbon material with a molecular oxygen containing gas, and an aqueous stream comprising recycled wastewater and less than 3.0 percent by weight acetic acid, wherein prior to being added to the aqueous stream at least a portion of the recycled wastewater is stripped of undesirable components in a stripping column using a stripping gas which includes a waste gas stream; (B) contacting the mixed product gas with the aqueous stream in the absorption tower to form an aqueous (meth)acrylic acid stream; (C) feeding the aqueous (meth)acrylic acid stream to a distillation column, wherein it is subjected to azeotropic distillation in the presence of at least one distillation solvent to form a (meth)acrylic acid solution substantially free of water.

In a third aspect of the present invention, there is provided a process for preparing (meth)acrylic acid, including the steps of: (A) stripping at least a portion of a recycled wastewater stream in a stripping column, using a stripping gas which includes an absorber off-gas, to form an aqueous stream having less than 3.0 percent by weight acetic acid; (B) feeding (i) a mixed product gas from the catalytic oxidation of at least one hydrocarbon material with a molecular oxygen containing gas, and (ii) the aqueous stream to an absorption tower; (C) contacting the mixed product gas with the aqueous stream in the absorption tower to form an aqueous (meth)acrylic acid stream; (D) feeding the aqueous (meth)acrylic acid stream to a distillation column, wherein it is subjected to azeotropic distillation in the presence of at least one distillation solvent to form a (meth)acrylic acid solution substantially free of water.

In a fourth aspect of the present invention, there is provided a process for preparing (meth)acrylic acid, including the steps of (A) feeding to an absorption tower a mixed product gas from the catalytic oxidation of at least one hydrocarbon material with a molecular oxygen containing gas, and an aqueous stream comprising recycled wastewater and less than 3.0 percent by weight acetic acid, wherein prior to being added to the aqueous stream at least a portion of the recycled wastewater stream is stripped of undesirable components in a stripping column using a stripping gas which includes a waste gas stream; (B) contacting the mixed product gas with the aqueous stream in the absorption tower to form an aqueous (meth)acrylic acid stream; (C) stripping light ends from the aqueous (meth)acrylic acid stream; and (D) feeding the aqueous (meth)acrylic acid stream to a distillation column, wherein it is subjected to azeotropic distillation in the presence of at least one distillation solvent to form an (meth)acrylic acid solution substantially free of water.

Figure 1:
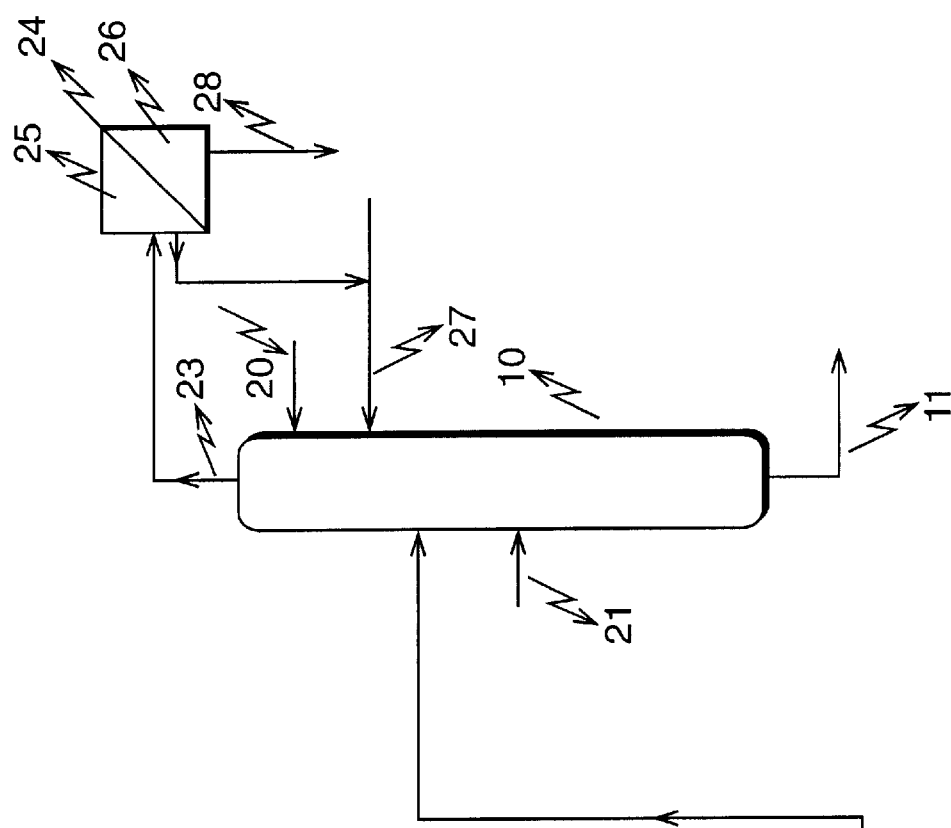
FIG. 1 depicts a flow chart showing one embodiment of the process of the present invention.
Figure 1:
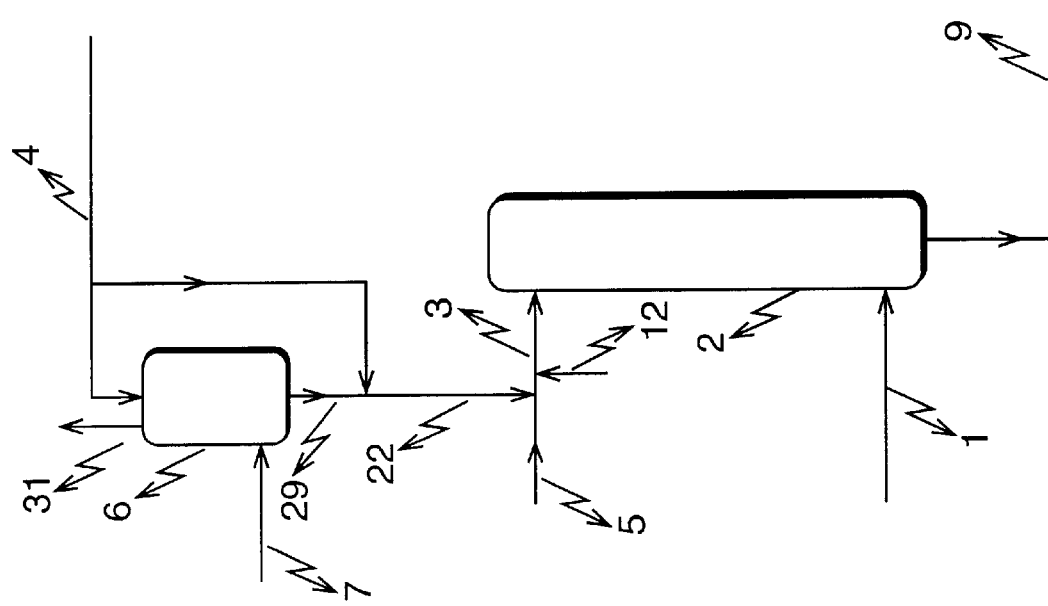

Throughout this specification and claims, unless otherwise indicated, references to percentages are by weight percent and all temperatures are in degree centigrade.

It is also to be understood that for purposes of this specification and claims that the range and ratio limits, recited herein, are combinable. For example, if ranges of 1–20 and 5–15 are recited for a particular parameter, it is understood that ranges of 1–15 or 5–20 are also contemplated.

Also, the term "major amount" is understood to mean greater than 50 percent by weight of the total composition. The term "minor amount" is understood to mean less than 50 percent by weight of the total composition.

The term "wastewater" is understood to mean any water stream having impurities and/or additives contained therein. In a like manner, the term "waste gas" is understood to mean a gas or mixture of gases having impurities and/or additives contained therein.

The term "(meth)acrylic acid" is understood to encompass both acrylic acid and methacrylic acid.

The process of the present invention will be initially described with reference to FIG. 1. Further reference to FIGS. 2 and 3 will be made to describe various other embodiments of the invention. Also, although the present invention is described following in terms of a process for preparing acrylic acid, it is to be understood that the invention encompasses preparation of methacrylic acid also.

As recited above, the process of the present invention for preparing (meth)acrylic acid includes feeding a mixed product gas 1 from the vapor phase catalytic oxidation of at least one hydrocarbon material with a molecular oxygen containing gas to an absorption tower 2.

The mixed product gas is generally obtained by the vapor phase catalytic oxidation of a hydrocarbon material with a molecular oxygen containing gas in the presence of a suitable oxidation catalyst. The vapor phase catalytic oxidation of a hydrocarbon material to acrolein and/or acrylic acid as well as reactors, catalysts, and processes for performing the same are generally known in the art and are described, for instance in U.S. Pat. Nos. 4,203,906; 4,256,783; 4,365,087; 4,873,368; 5,161,605; 5,177,260; 5,198,578; 5,739,391; 5,821,390, and co-pending U.S. patent application Ser. No. 09/244182.

Depending on the reactants fed to the reactor, the mixed product gas generally includes inert gas(es), including but not limited to, nitrogen, helium, argon, etc.; acrylic acid; unreacted hydrocarbon reactants, including but not limited to, propylene, acrolein, propane, etc.; steam, and molecular oxygen containing reactants, including but not limited to, air, oxygen, etc.; reaction byproducts, including but not limited to, acetic acid, formaldehyde, maleic acid, and other organics; as well as $CO_2$, CO and $H_2O$.

Generally, the composition of the mixed product gas feed 1 includes from 5 to 30 percent by weight acrylic acid, from 0.1 to 3.0 percent by weight acetic acid, from 0.02 to 0.2 percent by weight acrolein, from 30 to 95 percent by weight inert gas, and from 1 to 30 percent by weight steam.

The process of the present invention for preparing acrylic acid also includes feeding an aqueous stream 3 which includes recycled wastewater to the absorber 2. The wastewater may be any wastewater suitable for use in absorbing acrylic acid from an acrylic acid mixed product gas and may be from any source. Consequently, it is not necessary that the wastewater be derived from the same acrylic acid process stream into which it is recycled. Rather, the wastewater may be derived from one acrylic acid process stream and recycled into another. Suitable examples of wastewater include, but are not limited to, wastewater derived from dehydration of acrylic acid, other aqueous distillates, and raffinates. In a like manner, it is not necessary that the wastewater be derived from an acrylic acid wastewater stream. Accordingly, the wastewater may be derived from other chemical process wastewater streams, for example, from a (meth)acrylate process stream. Furthermore, the wastewater may be derived from a natural source such as a river, well, spring or the like.

The aqueous stream 3 may include any suitable amount of recycled waste water up to 100 weight percent recycled wastewater. Typically, the aqueous stream 3 will be a mixture of a wastewater stream 22 from an acrylic acid manufacturing process and an essentially pure water stream 5, e.g., deionized water. In one embodiment, the aqueous stream 3 includes a major amount of wastewater. In another embodiment, the aqueous stream 3 includes from 0.1 percent by weight to 100 percent by weight of wastewater. Preferably, the aqueous stream 3 contains 100 percent by weight wastewater. Regardless of how much recycled wastewater is utilized, the aqueous stream will contain a major amount of water and minor amounts of at least one of acrylic acid, acetic acid, or distillation solvent(s). Generally, the aqueous stream contains less than 3.0, preferably less than 2.0, more preferably less than 1.5 percent by weight acetic acid. In another embodiment, the aqueous stream is substantially free of distillation solvent(s) and/or acrylic acid.

As indicated in FIG. 1, all or a portion of wastewater stream 4 may be stripped of undesirable components before being introduced into aqueous stream 3. In one embodiment, wastewater stream 4 is stripped of undesirable components in a stripping column 6 using a stripping gas stream 7, which includes waste gas, to produce a stripped wastewater stream 29. Wastewater stream 29 is then fed to aqueous stream 3 as wastewater stream 22. Alternatively, a portion of wastewater stream 4 is stripped to form stripped wastewater stream 29 with the unstripped portion of wastewater stream 4 being combined with stripped wastewater stream 29 to form wastewater stream 22 which is then fed to aqueous stream 3. Finally, in an additional embodiment, all of wastewater stream 4 is introduced into aqueous stream 3 as wastewater stream 22 without being stripped. The amount of wastewater stream 4 which is stripped or unstripped will vary according to the amount of undesirable components in wastewater stream 4.

Figure 2:
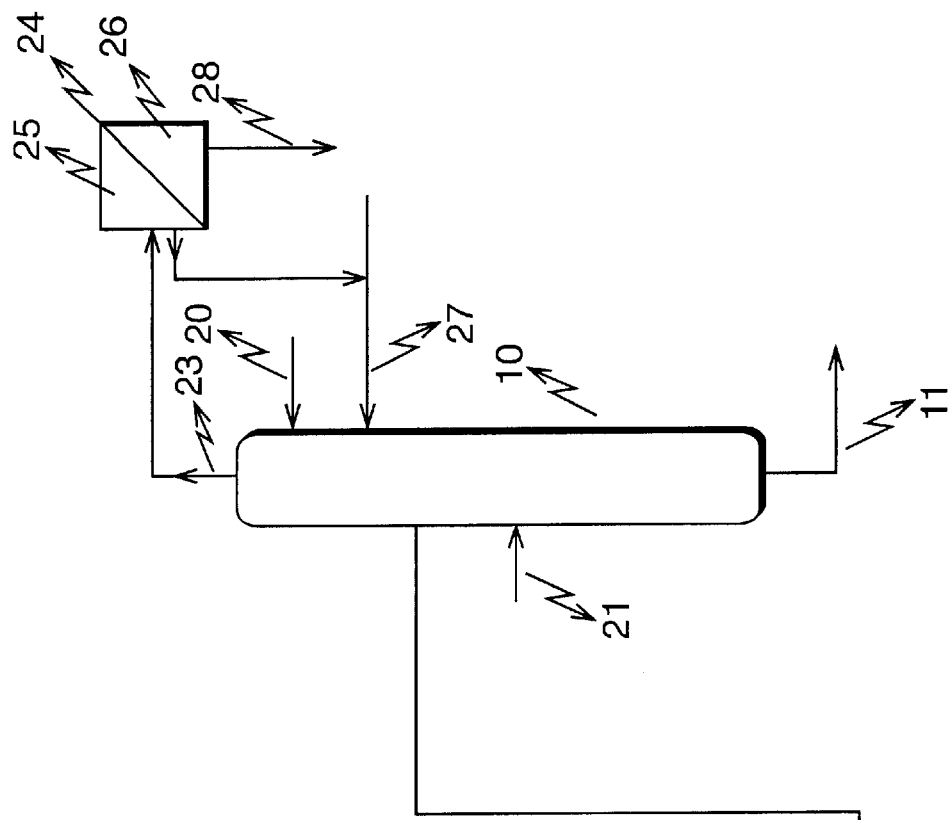
FIG. 2 depicts a flow chart showing a second embodiment of the process of the present invention.
Figure 2:
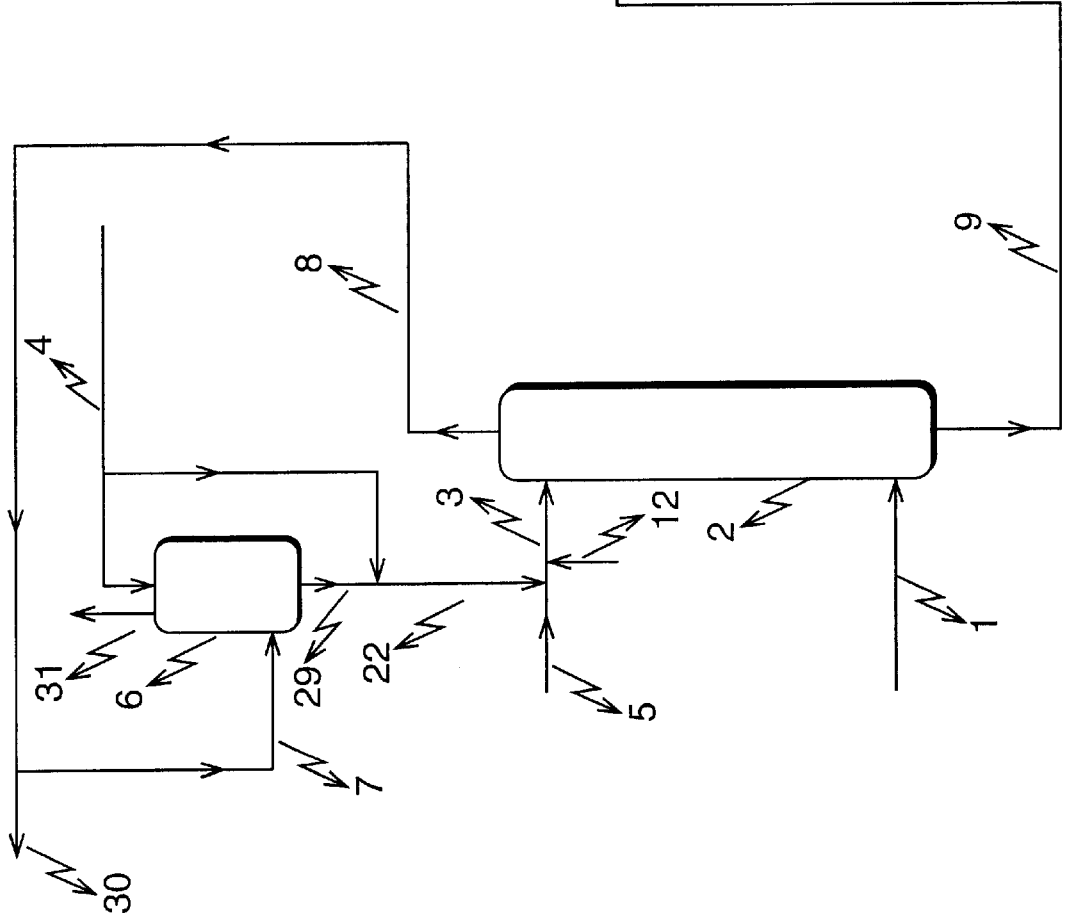

The stripping gas stream 7 may include, but not be limited to, combustion air and fresh air as well as waste gases. The waste gas stream may be any waste gas stream suitable for stripping undesirable components from a wastewater stream. Suitable examples include absorber off-gas streams, compressor suction vent gas streams, and stripping gas streams. Preferably, the waste gas stream is an absorber off-gas stream. Such an embodiment of the present invention is illustrated in FIG. 2 wherein the absorber off-gas stream 8 from the absorber 2 is fed to the stripping column 6 as stripping gas stream 7 to remove undesirable components from the wastewater stream 4 in the stripping column 6. The absorber off-gas stream 8 is typically split so that a portion, stream 30, is recycled to an oxidation reactor with the remainder used as a stripping gas 7.

The waste gas stream 31 from the stripper 6 is generally sent to waste treatment for incineration and/or oxidation and then released to the atmosphere.

Generally, the stripping waste gas has a water content of from 0 to 100, preferably 5 to 30, more preferably 8 to 20 weight percent and a temperature from 20 to 250, preferably 45 to 125, more preferably from 50 to 90 degrees Centigrade. The use of a portion of the absorber off gas stream 8 as a stripping gas 7 is advantageous because the absorber off gas emerges from the absorber with a sufficient heat and water content for adequately stripping undesirable components from the wastewater. Accordingly, treatment of a potential waste gas stripping stream, i.e., heating and adding or removing water, is avoided.

However, at times it may be desirable to either use other stripping gas streams such as air, combustion air, etc., either alone or in combination with an absorber off-gas stream. This may require additional heating of the stripping gas to obtain a proper operating temperature range. Also, additional heat may be required to increase the removal of organics from the wastewater stream. Consequently, a live steam sparge, external or internal reboilers, stripping gas feed pre-heater, or other methods known in the art of supplying additional heat to a stripping column may be utilized. In addition, there may be instances wherein additional momentum transfer within the stripping column is required. For example, where there is an increased pressure drop within the column and absorber pressure is insufficient to provide adequate momentum transfer. Consequently, devices such as a blower may be utilized to increase such momentum transfer.

The stripping column 6 may be any column suitable for stripping undesirable components from wastewater. Such columns are known in the art and include packed columns and tray containing columns.

In a further embodiment, the aqueous stream 3 includes a polymerization inhibitor introduced at the polymerization inhibitor feed 12. The polymerization inhibitor may include a water soluble or alcohol soluble polymerization inhibitor. Suitable examples include but are not limited to, hydroquinone; 4-methoxy phenol; 4-ethoxyphenol; 1,2-dihydroxybenzene; catechol monobutyl ether; pyrogallol; 4-aminophenol; 2-mercaptophenol; 4-mercaptophenol; 4-hydroxy-2,2,6,6-tetramethylpiperidinyloxy, free radical; 4-oxo-2,2,6,6-tetramethylpiperidinyloxy, free radical; 4-amino-2,2,6,6-tetramethylpiperidinyloxy, free radical; isomers thereof; derivatives thereof; mixtures of two or more thereof; or mixtures of one or more of the above with molecular oxygen.

In the absorber the mixed product gas 1 is contacted with the aqueous stream 3 to form an aqueous acrylic acid stream 9. The aqueous acrylic acid stream 9 formed generally includes from 20 to 95, preferably 35 to 90, and more preferably 50 to 80 percent by weight acrylic acid; from 80 to 5, preferably from 65 to 10, more preferably from 50 to 20 percent by weight water; and up to 8, preferably up to 6, more preferably up to 5 percent by weight acetic acid. Generally, the mixed product gas 1 is fed to the absorber at a temperature from 165 to 400, preferably 200 to 350, more preferably 250 to 325 degrees. The aqueous stream 3 is fed to the absorber at a rate of 0.1 to 1.0 pounds of aqueous per one pound of hydrocarbon material fed to the reactor depending on the desired concentration of acrylic acid to be recovered from the bottoms of the absorber 2. The absorber 2 may be any suitable absorber design known in the art.

The aqueous acrylic acid stream 9 is then fed to a distillation column 10 wherein it is subjected to azeotropic distillation in the presence of at least one distillation solvent to form an acrylic acid stream 11. The distillation column may be any suitable distillation column known in the art. For instance, a sieve tray, a dual flow tray design, or a packed column may be used.

The distillation solvent or solvents may be any solvent(s) suitable for the azeotropic distillation of an acrylic acid stream. In one embodiment, the solvent is substantially water insoluble, generally having a solubility in water at room temperature of 0.5 weight percent or less, preferably 0.2 weight percent or less. Suitable examples of such a water insoluble solvent include, but are not limited to heptane; heptene; cycloheptane; cycloheptene; cycloheptatriene; methylcyclohexane; ethylcyclopentane; 1,2-dimethylcyclohexane; ethylcyclohexane; toluene; ethylbenzene; ortho-, meta-, or para- xylene; trichloroethylene; trichloropropene; 2,3-dichlorobutane; 1-chloropentane; 1-chlorohexane; and 1-chlorobenzene. In another embodiment, the solvent is selected from ethyl acetate, butyl acetate, dibutyl ether, hexane, heptane, ethyl methacrylate, diethyl ketone, methyl propyl ketone, methyl isobutyl ketone, and methyl tert-butyl ketone. In a further embodiment, the distillation solvent is a mixed solvent which includes at least two solvents. Suitable examples of solvents useful in such mixed solvent include, but is not limited to, diethyl ketone, methyl propyl ketone, methyl isobutyl ketone, methyl tert-butyl ketone, isopropyl acetate, n-propyl acetate, toluene, heptane and methylcyclohexane. The preferred distillation solvent is toluene.

Figure 3:
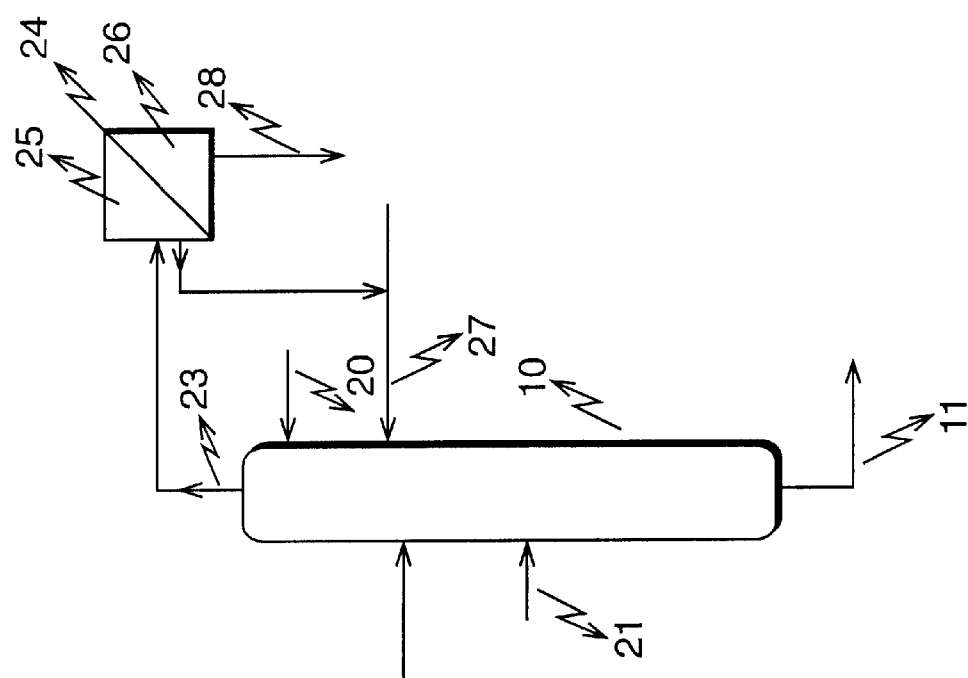
FIG. 3 depicts a flow chart showing a third embodiment of the process of the present invention.
Figure 3:
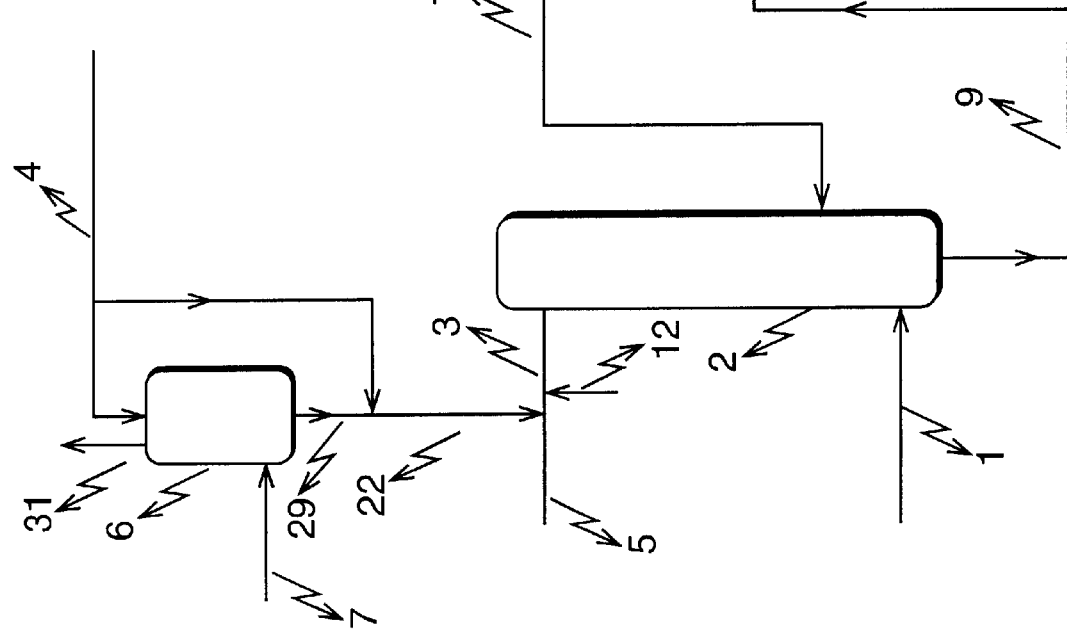

In one embodiment, as illustrated in FIG. 3, the aqueous acrylic acid stream 9 is fed to a light ends stripper column 13 before being fed to the distillation column 10. The light ends column 13 strips light ends, including but not limited to, acrolein, formaldehyde, acetaldehyde, propionaldehyde, methyl ether, and methyl vinyl ketone, from the aqueous acrylic acid stream 9. Generally, the stripping gas used is steam. Emerging from the bottom of the light ends column 13 is an acrylic acid stream 14 which is substantially free of light ends. The acrylic acid stream is then introduced into the distillation column 10. The stream 15 emerging from the top of the light ends column 13 is recycled back to the absorber 2 wherein some of the stripped acrolein is recovered in the absorber off gas and recycled back to the oxidation reactor thereby improving the yield of acrylic acid.

In a further embodiment, the aqueous stream 9 or 14 includes a polymerization inhibitor introduced at polymerization inhibitor feeds 20 and 21. Suitable inhibitors are as described above. In one embodiment, the polymerization inhibitor is 4-hydroxy-2,2,6,6-tetramethylpiperidinyloxy, free radical; derivatives thereof or mixtures of 4-hydroxy-2,2,6,6-tetramethylpiperidinyloxy, free radical with molecular oxygen. In an alternative embodiment, the polymerization inhibitor is a mixture of 4-hydroxy-2,2,6,6-tetramethylpiperidinyloxy, free radical; derivatives thereof or mixtures of 4-hydroxy-2,2,6,6-tetramethylpiperidinyloxy, free radical with at least one other inhibitor and molecular oxygen.

Certain distillation column designs, such as a sieve tray column, require use of a vapor phase polymerization inhibitor. Examples of suitable vapor phase inhibitors useful in the present invention include, but are not limited to, N-nitrosophenylhydroxylamine and salts thereof, nitric oxide, nitrosobenzene, and p-benzoquinone.

Emanating from the bottoms of the distillation column 10 is an acrylic acid stream 11 which is substantially free of water. Generally, the acrylic acid stream 11 has less than 1000, preferably less than 800, more preferably less than 500 ppm of water. The acrylic acid stream may also contain insubstantial amounts of at least one of the following: acetic acid, propionic acid, β-acryloxypropionic acid (AOPA), acrolein, furfural, benzaldehyde, maleic acid, maleic anhydride, protoanemonin, and acetaldehyde.

The acrylic acid stream 11 is generally sent to be used as a raw material in acrylic ester or acrylate polymer production. The acrylic acid may be used as is or be further processed, including but not limited, additional distillation to remove specific impurities and further processing to form various grades of acrylic acid.

The overhead distillate stream 23 emanating from the top of the distillation column 10 generally includes, but is not limited to, azeotropes of water, acetic acid, and/or acrylic acid with the distillation solvent. For instance, should toluene be utilized as a distillation solvent toluene/water, toluene/acetic acid, and toluene/acrylic acid azeotropes would be taken overhead in a two liquid phase system. The overhead distillate stream 23 is phase separated into organic and aqueous phases. The phase separation may be done by any means known in the art.

In one embodiment, the overhead distillate stream 23 is introduced into a tank 24 and allowed to phase separate into an organic phase 25 and an aqueous phase 26. The organic phase 25 predominantly includes the distillation solvent. The aqueous phase 26 includes, but is not limited to, acrylic acid, acetic acid, the distillation solvent and water. In one embodiment, the organic phase 25 is recycled back to the distillation column by way of the solvent feed line 27 so that the distillation solvent may be reused. Also, as indicated in FIG. 1, at least a portion of the aqueous phase 26 may be recycled 28 as wastewater directly to aqueous stream 3. Alternatively, as also indicated in FIG. 1, at least a portion of the aqueous phase 26 may be recycled 28 as wastewater directly to stripper 6 and then on to aqueous stream 3 after stripping. In another embodiment, at least a portion of the aqueous phase 26 may be recycled 28 as wastewater directly to aqueous stream 3 and at least a portion of the aqueous phase 26 may be recycled 28 as wastewater directly to stripper 6 and then on to aqueous stream 3 after stripping. In this embodiment the stripped wastewater stream 29 and unstripped wastewater stream 4 are combined as wastewater stream 22 and introduced into aqueous stream 3. It is to be understood that the aqueous phase 26 may be recycled, in part or completely, to another wastewater stream in another acrylic acid manufacturing process. Alternatively, part or all of the organic and aqueous phases may be diverted or treated and released to the environment.

The following Examples are provided as an illustration of the present invention.

EXAMPLE (a) Azeotropic Distillation with Toluene Solvent

An extended run of an azeotropic toluene distillation column was conducted at operating conditions using a 1 inch diameter, 30-tray Oldershaw column mounted on a bottoms reboiler pot sparged with air at a rate of 30 cc/min. The feed tray was at tray 15 and the control tray was at tray 18, both from the bottom. The distillation was operated at the following conditions:

215 mm Hg top pressure 155 g/hr total aqueous AA feed rate 333 g/hr toluene reflux rate 75° C. control tray temperature An aqueous acrylic acid feed composition was fed to the distillation column at tray 15 and toluene reflux was fed to the top tray at the rate indicated. The aqueous acrylic acid feed composition contained 67 weight percent acrylic acid, 1 weight percent β-acryloxypropionic acid (AOPA), 28 weight percent water, and 3 weight percent acetic acid, and 1 weight percent other minor components such as formaldehyde, formic acid, maleic acid, and hydroquinone polymerization inhibitor. The hydroquinone was available from Aldrich Chemical Co. of Milwaukee, Wis. Also, 4-hydroxy-2,2,6,6-tetramethylpiperidinyloxy, free radical polymerization inhibitor, available from Aldrich Chemical Co. of Milwaukee, Wis., was fed as a 0.08 weight percent aqueous solution into the aqueous acrylic acid feed at a rate of 5 grams/hour and p-benzoquinone vapor phase inhibitor, available from Aldrich Chemical Co. of Milwaukee, Wis., was fed as a 0.24 weight percent toluene solution to the top tray at a rate of 10 grams/hour. Furthermore, an additional stream of 4-hydroxy-2,2,6,6-tetramethylpiperidinyloxy, free radical was fed as a 0.34 weight percent aqueous solution to the top tray at a rate of 5 grams/hour. The inhibitor feeds resulted in an inhibitor levels in the column, based on bottoms, of 200 ppm of 4-hydroxy-2,2,6,6-tetramethylpiperidinyloxy, free radical, 316 ppm hydroquinone, and 650 ppm of p-benzoquinone.

The distillation ran smoothly for 99 hours. At the end of the run, the column and pot were clean, i.e., no polymerization of monomer detected.

Analysis by gas chromatography showed:

280 ppm HAc in the bottoms 0.2 ppm toluene in the bottoms 4 weight percent AOPA in the bottoms 96 weight percent acrylic acid in the bottoms less than 300 ppm water in the bottoms 1.6 wt % AA in the aqueous distillate Consequently, a suitable stream of crude acrylic acid was achieved. Aqueous distillates from this procedure were collected and used in part b following.

(b) Waste Gas Stripping of Wastewater

A stream of room temperature, dry air (6050 cc/min–433 g/hr) was heated to 67° C. to form a heated dry air stream. The heated dry air stream was then bubbled upwards through a 1 inch diameter, 10-tray Oldershaw column and contacted in countercurrent fashion with warm water (67° C.) running down the column. Approximately 97 g/hr of water were absorbed into the heated air stream and the resulting effluent from this column—water-saturated (18% water) air at 67° C.—resulted in an absorber off-gas (AOG) stream. The AOG was then fed to the bottom of a 1 inch diameter, 10-tray Oldershaw column and contacted in a countercurrent fashion with 76 g/hr of toluene column aqueous distillate fed to the top of the column. The aqueous distillate was collected from a toluene distillation procedure according to part a of this Example. The composition of the aqueous distillate was 88.8 wt % water, 2.0 wt % AA, 7.5 wt % HAc, 1.1 wt % formaldehyde, and 0.6 wt % formic acid.

The stripped aqueous distillate was collected (84 g/hr) and analyzed by gas chromatography. The analysis showed a collected stripped aqueous distillate containing 97.3 wt % water, 0.2 wt % AA, 2.1 wt % HAc, 0.2 wt % formaldehyde, and 0.1 wt % formic acid. In a like manner, the vapor effluent from the stripper was condensed, and the liquid condensate was collected (88 g/hr) and analyzed showing a collected liquid condensate containing 94.4 wt % water, 0.9 wt % AA, 3.9 wt % HAc, 0.6 wt % formaldehyde, and 0.2 wt % formic acid.

Material balance analysis showed that a 79% removal of AA, 66% of HAc, 84% of formaldehyde, and 56% of formic acid from the toluene column aqueous distillate was achieved.

We claim:

1. A process for preparing (meth)acrylic acid, comprising:

(A) feeding to an absorption tower
        (i) a mixed product gas from the catalytic oxidation of at least one hydrocarbon material with a molecular oxygen containing gas, and
        (ii) an aqueous stream comprising recycled wastewater and less than 3.0 percent by weight acetic acid;

(B) contacting the mixed product gas with the aqueous stream in the (C) absorption tower to form an aqueous (meth)acrylic acid stream; and (C) feeding the aqueous (meth)acrylic acid stream to a distillation column, wherein it is subjected to azeotropic distillation in the presence of at least one distillation solvent to form a (meth)acrylic acid solution substantially a free of water;

wherein at least a portion of the recycled wastewater is stripped of undesirable components in a stripping column using a stripping gas which comprises a waste gas stream prior to feeding the recycled wastewater to the absorption tower.

2. The process of claim 1, wherein the stripping gas is an absorber off-gas stream.

3. The process of claim 1, wherein the aqueous (meth) acrylic acid stream is stripped in a light ends stripper before being fed to the distillation column.

4. The process of claim 1, wherein the aqueous stream is 100 percent by weight wastewater.

5. The process of claim 1, wherein the at least one distillation solvent is toluene.

6. The process of claim 1, further comprising:

(i) phase separating overheads from the distillation column;

(ii) recycling the organic phase back to the distillation column; and (iii) recycling at least a portion of the aqueous phase as wastewater to the aqueous stream.

7. The process of claim 1, wherein at least one polymerization inhibitor selected from the group hydroquinone; 4-methoxyphenol; 4-ethoxyphenol; 1,2-dihydroxybenzene; catechol monobutyl ether; pyrogallol; 4-aminophenol; 2-mercaptophenol; 4-mercaptophenol; 4-hydroxy-2,2,6,6-tetramethyl piperidinyloxy, free radical; 4-oxo-2,2,6,6-tetramethylpiperidinyloxy, free radical; 4-amino-2,2,6,6-tetramethylpiperidinyloxy, free radical; isomers thereof; derivatives thereof, mixtures of two or more thereof; or mixtures of one or more of the above with molecular oxygen is added to the absorber.

8. The process of claim 1, wherein at least one polymerization inhibitor selected from the group hydroquinone; 4-methoxyphenol; 4-ethoxyphenol; 1,2-dihydroxybenzene; 2-methoxyphenol; p-benzoquinone; phenothiazine; pyrogallol; t-butyl catechol; 4-aminophenol; 2-aminophenol; di-t-butyl nitroxide; 2,2,6,6-tetramethylpiperidinyloxy, free radical; 4-hydroxy-2,2,6,6-tetramethyl piperidinyloxy, free radical; 4-oxo-2,2,6,6-tetramethylpiperidinyloxy, free radical; 4-amino-2,2,6,6-tetramethylpiperidinyloxy, free radical; 4-ethanoyl-2,2,6,6-tetramethylpiperidinyloxy, free radical; 2,2,5,5-tetramethylpyrrolidinyloxy, free radical; isomers thereof; derivatives thereof; mixtures of two or more thereof; or mixtures of one or more of the above with molecular oxygen is added to the distillation column.

* * * * *